United States Patent [19]

Smiles et al.

[11] Patent Number: 4,959,210
[45] Date of Patent: Sep. 25, 1990

[54] TREATMENT OF GENITAL WARTS WITH A COMBINATION OF LIQUID NITROGEN AND RECOMBINANT DNA HUMAN ALPHA INTERFERON

[75] Inventors: Kenneth A. Smiles, Windsor, N.J.; Edwin A. Peets, New York; Daniel J. Tanner, Brooklyn, both of N.Y.

[73] Assignee: Schering Corporation, Kenilworth, N.J.

[21] Appl. No.: 265,612

[22] Filed: Nov. 1, 1988

[51] Int. Cl.$^5$ .............................................. A61K 37/66
[52] U.S. Cl. ................................... 424/85.7; 424/85.4
[58] Field of Search ............................. 424/85.4, 85.7

[56] References Cited

U.S. PATENT DOCUMENTS 4,286,690 9/1981 Pestka et al. ..................... 260/112 R
4,503,035 3/1985 Pestka et al. ........................... 424/85

OTHER PUBLICATIONS

Ghosh, Britain Journal of Venereal Diseases, vol. 53, pp. 49–53, 1977.
Silva et al., J. Am. Acad. & Dermatology, vol. 13, 1985, pp. 457–463.
Eron et al., New Eng. J. Med., vol. 315, pp. 1059–1064, 1986.
Ferenczy et al., The NEJM 313, 784–788 (1985).
Rubenstein, Biochem. Biophys. Acta 695, 5–16 (1982).
Nagata et al., Nature 284, 316–320 (1980).
Smiles et al., The Biology of the Interferon System 1986, Cantell et al., Editor, Dordrecht, Martinus Mijhoff Publishers, 493–501 (1987).
Friedman–Kien et al., JAMA 259, 533–538 (1988).
Gall et al., Obstet Gynecol 67, 643 (1986).

*Primary Examiner*—Blondel Hazel
*Attorney, Agent, or Firm*—Thomas D. Hoffman; Gerald S. Rosen

[57] ABSTRACT

Condylomata Acuminata infections (anogenital warts) are treated in infected patients by administering liquid nitrogen and immediately thereafter beginning administering recombinant DNA human alpha interferon thrice a week for three weeks.

The interferon exemplified is recombinant DNA human interferon alfa-2b in which $1.0 \times 10^6$ International Units are administered by injection to each lesion.

The liquid nitrogen is the cryosurgical agent exemplified and it is topically administered to each lesion by conventional means.

10 Claims, No Drawings

TREATMENT OF GENITAL WARTS WITH A COMBINATION OF LIQUID NITROGEN AND RECOMBINANT DNA HUMAN ALPHA INTERFERON

BACKGROUND

1. Field of the Invention

This invention relates to a method of treating condyloma acuminatum, generally referred to as genital warts or anogenital warts, with a combination of cryosurgery and recombinant DNA human alpha interferon (hIFN-α). As a result of the combination treatment, the time for patients to have recurrence is significantly prolonged when compared to those treated with cryosurgery alone.

2. Prior Art

Condyloma acuminatum is a venereal disease caused by human papilloma viruses (HPV), including, e.g. Types 6 and 11. The disease is usually referred to as genital warts or anogenital warts. The incidence of the disease is increasing and there is evidence linking HPV infections to genitourinary neoplasms.

Liquid nitrogen is one of the common cryosurgical treatments for condyloma acuminatum. It is topically applied and cryosurgically removes the lesions. Results of such treatment can be temporary and evidence exists that epithelial tissue surrounding the lesion may retain the HPV causative organism causing recurrence of the lesions.

Thus, cryosurgery causes local tissue destruction, but its efficacy is limited and recurrence frequently occurs within a month. As discussed by Ferenczy et al., The New England Journal of Medicine 313; 784-788 (1985), who used laser therapy, the HPV is present in clinically and histologically normal squamous epithelium beyond areas treated destructively. Such presence of the virus in the epithelium was shown to correlate strongly with the risk of recurrence.

Human alpha interferon is a naturally occurring mixture of at least eleven compounds including those designated alpha-1 interferon and alpha-2 interferon. Alpha interferon exhibiting biological properties similar to those of naturally occurring human leukocyte interferon can be made by recombinant methods.

A number of alpha interferon species or components are known and are usually designated by a numeral and letter after the Greek letter alpha. Human alpha-1 interferon is one species contemplated for use in this invention as are the species designated human alpha-2 interferons. Under USAN, recombinant DNA human alpha-2 interferons are designated Interferon Alfa-2a, which can be made as disclosed in Rubenstein, Biochem. Biophys. Acta 695, 5-16 (1982), and Interferon Alfa-2b. Interferon Alfa-2b is the preferred species for use in this invention and is a recombinant DNA human alpha interferon. Also suitable is recombinant DNA human interferon alfa-2a.

Human interferon alfa-2b can be produced in bacteria and other microorganisms using recombinant DNA techniques including those disclosed in Nagata et al. Nature, 284, 316-320 (1980), European Patent No. 32,134 and U.S. Pat. No. 4,289,690. Various alpha interferon species are disclosed in U.S. Pat. No. 4,503,035. The preferred recombinant DNA human interferon alfa-2b used in this invention is also denoted herein as "hIFNα-2b". Intralesionally administered interferon has been shown to clear about one third of cases of condylomata acuminata when given three times weekly for three weeks as indicated in Eron et al., New England Journal of Medicine 15, 1059-1064, (1986) and Smiles et al., The Biology of the Interferon System 1986, Cantell et al. editor, Dordrecht, Martinus Mijhoff Publishers, 493-501 (1987). Friedman-Kien et al., JAMA 259, 533-538 (1988) reported that intralesional interferon has been shown to clear about two-thirds of cases when given twice weekly for up to eleven weeks.

SUMMARY OF THE INVENTION

This invention relates to a method of treating condylomata acuminata with a combination of cryosurgery and injectable interferon. This invention provides in its preferred aspects, methods for treating condylomata acuminata utilizing (1) a cryosurgery agent and (2) a parenteral (intralesional) solution of interferon.

The cryosurgical agent is applied with either a large cotton swab or a spraying device which sprays the cryosurgical agent onto the lesions either directly or through a tube surrounding the lesion or using a probe, depending on the location of the lesion(s). Suitable cryosurgical agents are liquid carbon dioxide, and liquid nitrogen, with liquid nitrogen preferred. An effective amount of the cryosurgical agent is applied topically to each lesion preferably once, although more frequent applications may be necessary, taking up to about fifteen seconds to apply per lesion using conventional means.

The interferon therapy is begun after application of the cryosurgical agent, e.g. liquid nitrogen. The intralesional interferon solution preferred for use in this invention contains a sufficient amount of interferon to provide about 1 0 Mu per lesion ($1.0 \times 10^6$ International Units), although amounts from $1 \times 10^4$ to $1 \times 10^7$ are suitable. The HIFNα-2b is administered three times a week to the site of the genital warts via any of the accepted modes of administration for interferon. These methods include parenteral, topical, depot and transdermal. Intralesional injection is preferred.

Injectable pharmaceutically acceptable and administerable alpha interferon is prepared by dissolving, dispersing, etc., the interferon in a pharmaceutically acceptable carrier, such as, for example, water, saline, aqueous dextrose, glycerol, ethanol, and the like to form a solution or suspension for injection. If desired, the injectables composition to be administered may also contain minor amounts of nontoxic auxiliary substances such as wetting or emulsifying agents, preservatives, stabilizers, pH buffering agents, and the like, for example, sodium acetate or sorbitan monolaurate. Actual methods of preparing such dosage forms are known, or will be apparent, to those skilled in this art; for example, see Remington's Pharmaceutical Sciences, Mack Publishing Company, Easton, Penna., 15th Edition (1975). The composition or formulation to be administered will, in any event, contain a quantity of interferon in an amount effective to achieve the desired effect in the subject being treated. A suitable human alpha interferon injectable composition is available as Intron ® A from Schering-Plough Corporation, Kenilworth, N.J. The commercial composition contains human interferon alfa-2b, glycine, di- and mono-basic sodium phosphate and human serum albumin.

Based on the judgement of the attending clinician, the amount of active components administered and treatment regimen will, of course, be dependent on the subject being treated, the severity of the condylomata acuminata and the tolerance of the patient to the treatment regimen.

Administration of interferon in combination with treatment with a cryosurgical agent extends significantly the time to recurrence of the lesions in patients where recurrence is manifested

DETAILED DESCRIPTION

The following is a description of the clinical protocol utilized.

STUDY SYNOPSIS

The clinical study was a randomized, third party blinded (blind evaluator), single center, parallel group design in which a total of 77 patients were evaluated.

All patients had three condylomata acuminata lesions treated and evaluated. The patients were randomized so that all three lesions (test sites) selected for treatment in a given individual received either one topical application of liquid nitrogen followed by intralesional injections of interferon, or all three test sites received only one topical application of liquid nitrogen. The test sites were treated either with interferon thrice weekly for three consecutive weeks with the first injection immediately following the initial topical application of liquid nitrogen or only the single application of liquid nitrogen.

The amount of interferon administered was about $1.0 \times 10^6$ International Units per lesion of alfa-2b interferon, the amount of liquid nitrogen administered was sufficient to cover the lesion The size and symptomatology of the test sites were evaluated weekly for four weeks then every four weeks for 20 weeks At each evaluation after the first, change of each test site relative to the condition at entry into the study was estimated and adverse reactions noted. Blood chemistry, hematology and urinalysis were also conducted to check for systemic side effects.

A third party evaluator, i.e. one who was unaware of the treatment assignments, made all efficacy and safety evaluations.

STUDY DESIGN

This was a randomized, third party blinded (blind evaluator), parallel group study designed to determine if treating condyloma acuminatum (genital warts caused by the human papilloma virus) once with liquid nitrogen immediately followed by injections thrice weekly for three weeks of recombinant DNA human alpha interferon ($1.0 \times 10^6$ IU) intralesionally is more efficacious than liquid nitrogen alone. 77 patients with anogenital warts were evaluated in the study. 39 of the patients were treated with the combination of hIFNα-2b and liquid nitrogen whereas 38 were treated with liquid nitrogen alone.

In the study three lesions (venereal warts) with their smallest average volume of about 4 mm$^3$ and their largest volume about 296 mm$^3$ were selected as test sites. The test sites were outlined with a skin marking pen and designated A, B and C respectively. Each test site was evaluated, photographed and the location documented on a dermogram.

For a given patient, each of the test sites received either (1) sufficient topically applied liquid nitrogen to cover the lesions (only once and on the first day) immediately followed by an intralesional injection of 0.10 cc containing $1.0 \times 10^6$ International Units hIFNα-2b or (2) topical application of liquid nitrogen only once and on the first day of treatment. The interferon injection was made into the base and substance of the test site lesions using a 30 gauge needle. Although different concentrations of the interferon can be used, the dosage used is preferred since it is efficacious.

During the three weeks treatment period, the size and global response of each test site were evaluated once a week immediately prior to the first treatment day of that week. Those patients receiving interferon were treated three times a week for three consecutive weeks. Photographs of the test sites were taken at these times to document changes in disease status or local intolerance to the treatments. Also, at each visit all symptoms and adverse reactions which occurred since the previous evaluations were recorded.

Post treatment evaluations of the test sites were made, during which no additional treatments were given, on Day 1 of weeks 4, 8, 12, 16, 20 and 24. During the evaluation, the size of the lesions, side effects and global responses were observed and the test sites were photographed.

DRUG SUPPLIES

Recombinant DNA human interferon alfa-2b was supplied by Schering Corp., Kenilworth, N.J. in vials containing $1.0 \times 10^7$ International Units of recombinant DNA human inteferon alfa-2b in a lyophilized powder containing glycine, phosphate buffers (USP) and human serum albumin (HSA). One milliliter of sterile Water for Injection (U.S.P.) was added to each vial just prior to use. The powder was dissolved in the water. For each injection 0.10 cc of the solution (isotonic) was drawn into a syringe and injected. 0.10 cc of the solution provides $1.0 \times 10^6$ IU of the interferon.

Liquid nitrogen was obtained from Airco, Inc. Minneapolis, Minn.

EFFICACY EVALUATIONS

Just prior to each subject's first treatment, the volume of each test sites was estimated in cubic millimeters. The patient rated the symptoms, e.g. burning, itching and pain for each test site as follows: 1=mild, 2=moderate, 3=severe. Color photographs of the test sites were taken at an appropriate magnification.

On day 1 of weeks 2 and 3, prior to any treatment that day, the size of each test site was again recorded along with a global evaluation of the change in the condition of each test site which occurred since the start of treatment, using the criteria in the six point scale shown in Table 1. The global evaluation of change for each test site was based on the criteria listed in Table 1 and also reflected the blind evaluator's overall observations regarding flattening, change in volume, change in consistency or other physical characteristics of that lesion. Photographs were taken of the test sites at each evaluation.

Post treatment evaluations were carried out after the last treatment on day 1 of study weeks 4, 8, 12, 16, 20 and 24. The evaluations consisted of determining size, evaluating global response and photographing the test sites.

The following Table 1 is the scale for global evaluation of change in condylomata acuminata lesions.

TABLE 1

Scale for Global Evaluation of Change in Condylomata

| Score | Descriptive Term | Definition |
|---|---|---|
| 1 | Cleared | 100% clearance of the lesion |
| 2 | Marked Improvement | 75% to 100% reduction in lesion mass |
| 3 | Moderate Improvement | 50% to 75% reduction in lesion mass |
| 4 | Slight Improvement | 50% reduction in lesion mass |
| 5 | No Change | No change from baseline evaluation |
| 6 | Exacerbation | Increase in lesion mass |

The results of the study are tabulated in the following tables.

The data in Table 2 show that in each week after the second the combination treatment resulted in more patients having all of their test sites cleared of lesions than liquid nitrogen treated patients. More patients in the combination group remained clear of lesions for a longer period of time then those treated with liquid nitrogen alone. Of the patients that did not return for all the post-treatment evaluations, a significantly larger number were classed as treatment failures in the liquid nitrogen group.

The data in Table 3 show that more patients had a greater percent reduction in the size of lesions when treated with interferon plus liquid nitrogen than those treated with only liquid nitrogen, particularly after week 2 and maintained the percent reduction to week 24.

In all weeks the combined treatment resulted in more lesion reduction and later recurrence, if any.

Side effects occurred in more patients treated with interferon and liquid nitrogen than with liquid nitrogen alone; however, the side effects attributed to interferon were generally mild to moderate flu-like symptoms and were not medically serious. Local morbidity was not increased in any important way by the concomitant use of interferon and liquid nitrogen. The side effects had very little influence on the clinical program.

Clearly the above results in the Tables show that the combination treatment of this invention is more efficacious than treatment with liquid nitrogen alone.

We claim:

1. A method of treating condylomata acuminata infections in patients in need of such treatment comprising administering to each lesion an effective amount of a cryosurgical agent, followed by administration to each lesion immediately thereafter an effective amount of human alpha interferon.

TABLE 2

| Treatment | Week | No. of Patients | Number of Test Site Lesions (Patients) | | | |
|---|---|---|---|---|---|---|
| | | | 0 | 1 | 2 | 3 |
| Liquid Nitrogen plus Interferon | 1 | 39 | 0 | 0 | 0 | 39 |
| | 2 | 39 | 6 | 6 | 8 | 19 |
| | 3 | 39 | 12 | 10 | 2 | 15 |
| | 4 | 39 | 19 | 10 | 1 | 9 |
| | 8 | 37 | 16 | 6 | 4 | 11 |
| | 12 | 32 | 17 | 5 | 3 | 7 |
| | 16 | 28 | 18 | 2 | 3 | 5 |
| | 20 | 23 | 19 | 1 | 0 | 3 |
| | 24 | 23 | 18 | 2 | 1 | 2 |
| Liquid Nitrogen | 1 | 38 | 0 | 0 | 0 | 38 |
| | 2 | 38 | 9 | 2 | 2 | 25 |
| | 3 | 36 | 9 | 6 | 6 | 15 |
| | 4 | 38 | 9 | 8 | 9 | 12 |
| | 8 | 32 | 8 | 8 | 10 | 6 |
| | 12 | 21 | 7 | 3 | 7 | 4 |
| | 16 | 17 | 6 | 5 | 4 | 2 |
| | 20 | 9 | 4 | 3 | 2 | 0 |
| | 24 | 10 | 5 | 3 | 2 | 0 |

TABLE 3

Percent Reduction of Size of Lesions at Test Sites from the Pre-treatment Measurements (Patients)

| Treatment | No. of Patients | Week | 0 | 0-25 | 26-50 | 51-75 | 76-99 | 100 |
|---|---|---|---|---|---|---|---|---|
| Liquid Nitrogen plus Interferon | 39 | 2 | 1 | 1 | 5 | 9 | 18 | 6 |
| | 39 | 3 | 1 | 1 | 2 | 4 | 19 | 12 |
| | 39 | 4 | 1 | 0 | 1 | 2 | 16 | 19 |
| | 37 | 8 | 5 | 0 | 4 | 3 | 9 | 16 |
| | 32 | 12 | 2 | 0 | 3 | 3 | 7 | 17 |
| | 28 | 16 | 1 | 1 | 3 | 2 | 3 | 18 |
| | 23 | 20 | 1 | 1 | 1 | 1 | 0 | 19 |
| | 23 | 24 | 2 | 0 | 0 | 2 | 1 | 18 |
| Liquid Nitrogen | 38 | 2 | 1 | 2 | 7 | 10 | 9 | 9 |
| | 36 | 3 | 2 | 0 | 4 | 7 | 14 | 9 |
| | 38 | 4 | 1 | 3 | 3 | 6 | 16 | 9 |
| | 32 | 8 | 6 | 2 | 4 | 4 | 8 | 8 |
| | 21 | 12 | 3 | 1 | 2 | 2 | 6 | 7 |
| | 17 | 16 | 2 | 1 | 0 | 1 | 7 | 6 |
| | 9 | 20 | 0 | 0 | 0 | 1 | 4 | 4 |
| | 10 | 24 | 0 | 0 | 0 | 2 | 3 | 5 |

2. A method of claim 1 wherein the cryosurgical agent is liquid nitrogen.

3. A method of claim 1 wherein the human alpha interferon is recombinant human DNA interferon alfa-2b.

4. A method of claim 1 wherein the human alpha interferon is recombinant human DNA interferon alfa-2a.

5. A method of claim 1 wherein the treatment is sufficiently frequent and for a sufficient length of time to be efficacious.

6. A method of claim 1 wherein the treatment with said interferon is thrice a week for three weeks.

7. A method of claim 3 wherein the treatment with said interferon is thrice a week for three weeks.

8. A method of claim 4 wherein the treatment with said interferon is thrice a week for three weeks.

9. A method of claim 1 wherein the human alpha interferon is administered by intralesional injection and the liquid nitrogen is administered topically.

10. A method of claim 9 wherein the human alpha interferon is recombinant human DNA interferon alfa-2b.

* * * * *